United States Patent [19]

Speranza et al.

[11] Patent Number: 5,101,060

[45] Date of Patent: Mar. 31, 1992

[54] PAIRED MANNICH CONDENSATES OF ALKYL PHENOLS

[75] Inventors: George P. Speranza, Austin; Jiang-Jen Lin, Houston, both of Tex.

[73] Assignee: Texaco Chemical Company, White Plains, N.Y.

[21] Appl. No.: 615,104

[22] Filed: Nov. 19, 1990

[51] Int. Cl.$^5$ ................. C07C 217/44; C07C 255/37
[52] U.S. Cl. ..................................... 558/390; 564/346
[58] Field of Search .................... 558/390; 564/346

[56] References Cited

U.S. PATENT DOCUMENTS

| | | | |
|---|---|---|---|
| 1,919,301 | 7/1933 | Morton | 564/346 |
| 2,653,977 | 9/1953 | Craig et al. | 564/346 |
| 4,714,750 | 12/1987 | Grigsby, Jr. et al. | 564/367 |
| 4,927,912 | 5/1990 | Speranza et al. | 564/472 |

FOREIGN PATENT DOCUMENTS 0235066  4/1986  German Democratic Rep. .................... 564/346

Primary Examiner—Joseph P. Brust
Assistant Examiner—M. S. Gabilan
Attorney, Agent, or Firm—Jack H. Park; Kenneth R. Priem; Carl G. Ries

[57] ABSTRACT

Normally liquid final Mannich condensates prepared by reacting a para $C_1$–$C_{15}$ alkyl phenol with formaldehyde and a first polyoxyalkylene diamine to form an intermediate Mannich condensate that is reacted with formaldehyde and a second polyoxyalkylene diamine to form a final Mannich condensate, the first and second polyoxyalkylene diamines having the formula:

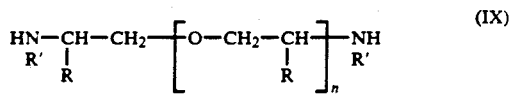

(IX)

wherein R represents hydrogen or methyl and R' represents an alkyl group containing 1 to 4 carbon atoms or cyanoethyl group, and n represents positive numbers having a value of 1 to about 6, the final Mannich condensate having the formula:

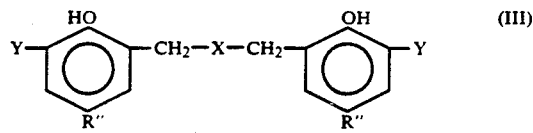

(III)

wherein X and Y are polyoxyalkylene amine groups derived from the first and second polyoxyalkylene diamines and formaldehyde.

9 Claims, No Drawings

PAIRED MANNICH CONDENSATES OF ALKYL PHENOLS

BACKGROUND OF THE INVENTION

1. Field of the Invention

This invention relates to Mannich condensates prepared from an alkyl phenol, formaldehyde and polyoxyalkylene diamines, as hereinafter defined.

More particularly, this invention relates to initial Mannich condensates prepared by reacting an alkyl phenol with formaldehyde and a first polyoxyalkylene diamine to provide an intermediate paired alkyl phenol Mannich condensate which is further reacted with formaldehyde and a second polyoxyalkylene diamine, as hereafter defined, in order to provide a paired final Mannich condensate of the present invention.

The intermediate Mannich condensates and the final Mannich condensates are useful as epoxy resin curing agents.

2. Prior Art

The Mannich reaction is a well-known reaction which has been extensively reviewed in the literature. See, for example, "The Mannich Reaction", *Org. Reactions* 1, 303 (1942) and "Advances in the Chemistry of Mannich Bases", "Methods in Synthetic Organic Chemistry-Synthesis", *Academic Press*, pp. 703-775, 1973.

Brennan et al. U.S. Pat. No. 4,485,195 discloses Mannich condensates prepared by reacting an alkyl phenol with formaldehyde, diethanolamine and a minor amount of melamine to provide products which can be alkoxylated for use in the preparation of fire retardant, rigid polyurethane foams.

Other Mannich condensates prepared by reacting alkyl phenols with formaldehyde and alkanolamines and melamine are disclosed in Brennan et al. U.S. Pat. No. 4,487,852, Brennan U.S. Pat. No. 4,489,178 and Brennan U.S. Pat. No. 4,500,655.

Waddill et al. U.S. Pat. No. 4,736,011 discloses Mannich condensates prepared by the reaction of an imidazole with formaldehyde and a polyoxyalkylene polyamine which are useful as curing agents for epoxy resins.

Becker U.S. Pat. No. 3,734,965 discloses phenolic resins prepared by condensing a polyoxypropylenepolyamine with phenol and an aldehyde.

Grigsby et al., in U.S. Pat. No. 4,714,750, describe the Mannich condensates prepared from 2,6-di-t-butylphenol, formaldehyde and a polyoxyalkyleneamine, i.e.:

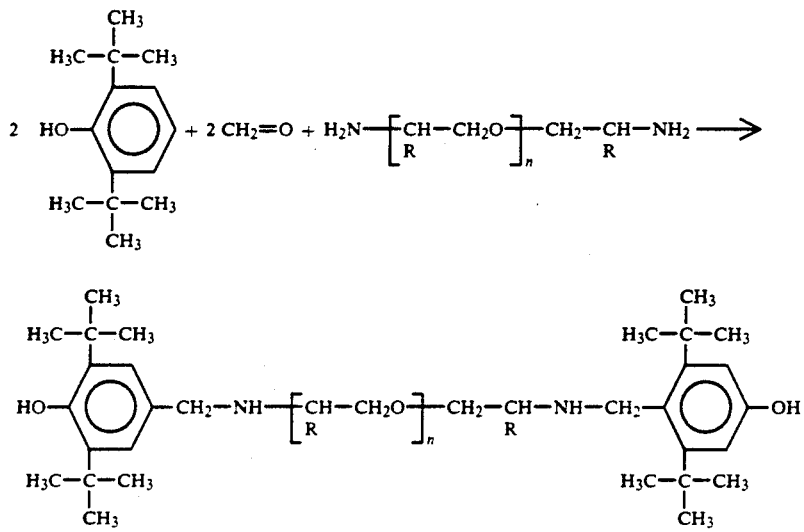

where: R=H or CH$_3$, and n=1 to 20.

Cyanoethylated derivatives of polyoxyalkylenepolyamines are disclosed in Rowton U.S. Pat. No. 3,666,788 and polyureas prepared by reacting the cyanoalkylated polyoxyalkylenepolyamines with an isocyanate are disclosed in Rowten et al. U.S. Pat. No. 3,714,128.

SUMMARY OF THE INVENTION

It has been discovered in accordance with the present invention that "paired" initial Mannich condensates can be prepared by reacting an alkyl phenol with formaldehyde and a first polyoxyalkylene diamine, such initial condensates having the formula:

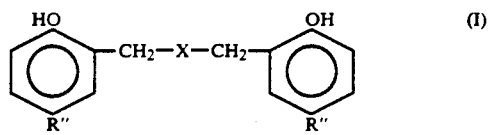

wherein:

R″ represents a straight chain or branched alkyl group containing from 1 to about 15 carbon atoms, and wherein X represents a polyoxyalkylene diamine group having the formula:

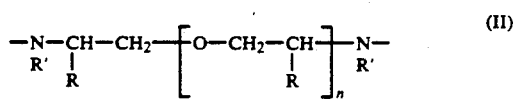

wherein:

R represents hydrogen or methyl,

R′ represents an alkyl group containing 1 to 4 carbon atoms or a cyanoethyl group, and n represents a positive number having a value of 1 to about 6.

It has been further discovered that "paired" initial alkyl phenol Mannich condensates of the type illustrated above (i.e., Mannich condensates containing two phenolic groups derived from the alkyl phenol that are separated by a diamine group derived from the formaldehyde and the first polyoxyalkylenediamine) are liquid at ambient temperatures.

It has also been discovered in accordance with the present invention that polyfunctional final Mannich condensates can be prepared by reacting the initial Mannich condensate with formaldehyde and a second polyoxyalkylene diamine to provide final Mannich condensates having the formula:

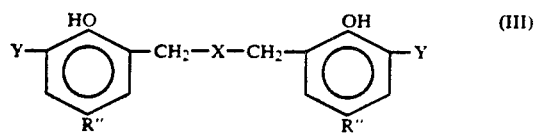

wherein Y represents a group having the formula:

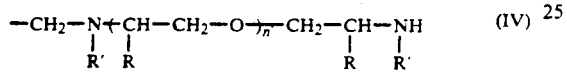

wherein:

n' represents a positive integer having a value of 1 to 6,

R represents hydrogen or methyl,

R' represents an alkyl group containing from 1 to 3 carbon atoms or a cyanoethyl group, and wherein X represents a polyoxyalkylene diamine group as defined in Formula II above.

DESCRIPTION OF THE INVENTION

The starting materials for the present invention are formaldehyde, a phenol having a $C_1$–$C_{15}$ alkyl group in the para position, a defined first class of polyoxyalkylene diamines and a defined second class of polyoxyalkylene diamines.

The First Class of Polyoxyalkylene Diamine Starting Materials

The first class of polyoxyalkylene diamine starting materials for the present invention are diamines having the formula:

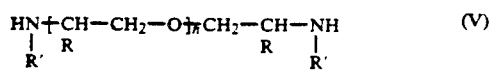

wherein n represents a positive number having a value of 1 to about 6,

R represents hydrogen or methyl, and

R' represents an alkyl group containing 1 to 4 carbon atoms or a cyanoethyl group.

N-alkyl derivatives of the polyoxypropylene diamines, wherein R' is an alkyl group containing 1 to 4 carbon atoms, that may be used as starting materials include, for example, the N-isopropyl derivatives of the polyoxypropylene diamines include isopropyl derivatives having the formula:

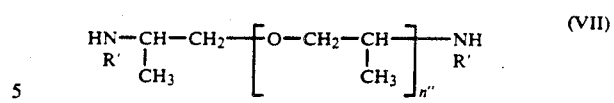

wherein:

R' represents an isopropyl group, and n'' represents a positive number having a value of 1 to about 6.

Cyanoethyl derivatives of polyoxypropylene diamines, wherein R' is a cyanoethyl group that may be used as starting materials include, for example, a cyanoethyl derivative of a polyoxypropylene diamine having the formula:

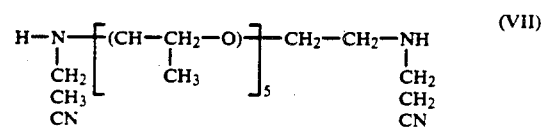

The Formaldehyde

Formaldehyde may be employed in any of its conventional forms. Thus, it may be, and preferably is, used in the form of an aqueous solution of formaldehyde such as "formalin" and may also be used in "inhibited" methanol solution as paraformaldehyde or as trioxane.

The Phenol Starting Material

The phenol should be a para alkyl phenol wherein the alkyl group contains 1 to 15 carbon atoms.

Representative examples of suitable phenols include compounds such as p-methyl phenol, p-ethyl phenol, p-propyl phenol, p-isopropyl phenol, the p-substituted n-butyl-, isobutyl- and tertiary butyl phenols, p-amyl phenol, p-decyl phenol, p-nonyl phenol, p-dodecyl phenol, p-pentadecyl phenol, etc. The phenols containing the larger alkyl groups are frequently prepared by reacting phenol with a dimer, trimer, tetramer or pentamer of propylene.

The Second Class of Polyoxyalkylene Diamine Starting Materials

The second class of polyoxyalkylene diamine starting materials to be used in accordance with the present invention, which may be the same or differnt members of the first class of polyoxyalkylene diamine starting materials are the polyoxyalkylene diamines of formula VI, i.e.

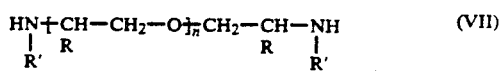

n represents a positive number having a value of 1 to about 6,

R represents hydrogen or methyl, and

R' represents an alkyl group containing 1 to 4 carbon atoms or a cyanoethyl group.

N-alkyl derivatives of the polyoxypropylene diamines, wherein R'''' is an alkyl group containing 1 to 4 carbon atoms, that may be used as starting materials include, for example, the N-isopropyl derivatives of the polyoxypropylene diamines include isopropyl derivatives having the formula:

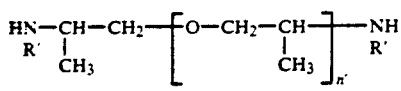

(VI)

wherein:

R' represents an isopropyl group, and n" represents a positive number having a value of 1 to about 6.

The isopropyl derivatives of polyoxyalkylene diamines having formula VI and formula IX may be prepared, for example, by the method disclosed and claimed in Speranza et al. U.S. Pat. No. 4,927,912, which issued May 22, 1990, and is entitled "Secondary Isopropyl Amines Derived from Oxyalkylene Diamines and Triamines".

Cyanoethyl derivatives of polyoxypropylene diamines that may be used as starting materials are those wherein R' is a cyanoethyl group and include, for example, a cyanoethyl derivative of a polyoxypropylene diamine having the formula:

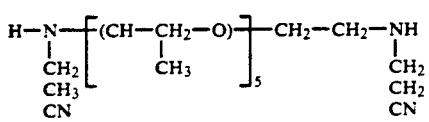

(VII)

Preparation of the Initial Mannich Condensates

In accordance with the present invention, the initial Mannich condensate is prepared by reacting a para aikyl phenol with formaldehyde and a first polyoxyalkylene diamine in the mole ratio of about 2:2:1 under Mannich reaction conditions including a temperature within the range of about 80° to about 150° C. for a period of time within the range of about 2 to about 8 hours. Pressure is not critical. The reaction is suitably conducted at atmospheric pressure although lower or higher pressures such as subatmospheric pressures or pressures of several atmospheres may be used. However, no particular advantage is obtained by using the lower or higher pressures.

The resultant reaction product will be composed principally of an initial Mannich condensate having the formula:

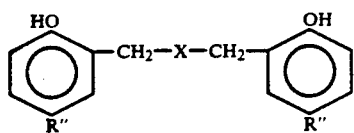

(I)

wherein:

R" represents a straight chain or branched alkyl group containing from 1 to about 15 carbon atoms, and X represents a polyoxyalkylene group having the formula:

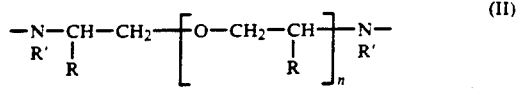

(II)

wherein:

R represents hydrogen or methyl,

R' represents an alkyl group containing 1 to 4 carbon atoms or a cyanoethyl group, and n represents a positive number having a value of 1 to about 6.

Preparation of the Final Mannich Condensate

In accordance with the present invention, a final Mannich condensate is prepared by reacting a second polyoxyalkylene diamine (which may be the same or different from the first polyoxyalkylene diamine) and formaldehyde with the initial Mannich condensate in the mole ratio of about 2:2:1 under Mannich condensation reaction conditions such as those recited above including a temperature within the range of about 80° to about 150° C. and a reaction time within the range of about 2 to about 8 hours.

Pressure is not critical. The reaction is suitably conducted at atmospheric pressure although lower or higher pressures such as subatmospheric pressures or pressures of several atmospheres may be used. However, no particular advantage is obtained by using a higher or a lower pressure.

The resultant reaction product will contain, as a principal component, a final Mannich condensate having the formula:

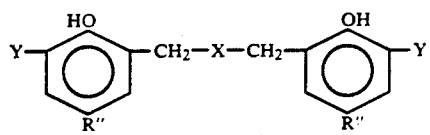

(III)

wherein Y represents a group having the formula:

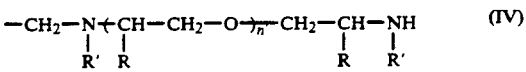

(IV)

wherein:

n' represents a positive integer having a value of 1 to 6, n represents a positive numbers having a value of 1 to about 6, R represents hydrogen or methyl, and R'" represents a straight or branched chain alkyl group containing from 1 to 4 carbon atoms or a cyanoethyl group, R" represents a straight chain or branched alkyl group containing from 1 to about 15 carbon atoms, and wherein X represents a polyoxyalkylene diamine group as defined in Formula II above.

We have found limitations to the method of synthesis of paired alkyl phenol Mannich condensates as disclosed herein and that the order of the addition of the reactants is very important.

For example, the preparation goes well for the initial bis-phenols:

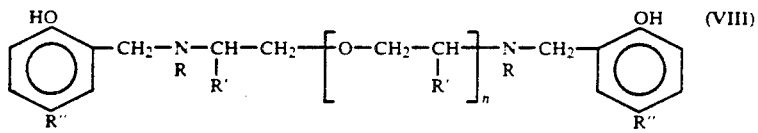

We have surprisingly discovered that the second step is very critical and that unexpected and unwanted results are obtained unless the second step is properly conducted.

For example, when R equals hydrogen in formula (VII) above, the synthesis of the unique compounds of the present invention is performed with comparative ease. Thus, in Experiment 6641-45, the reaction proceeded as follows:

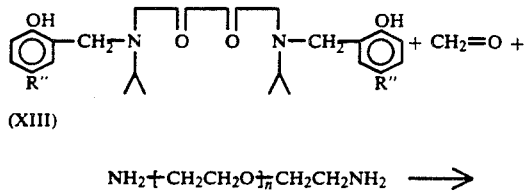

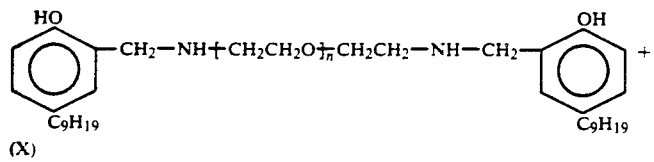

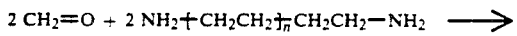

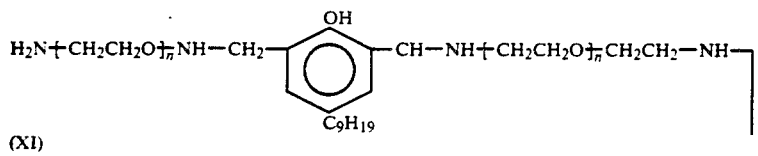

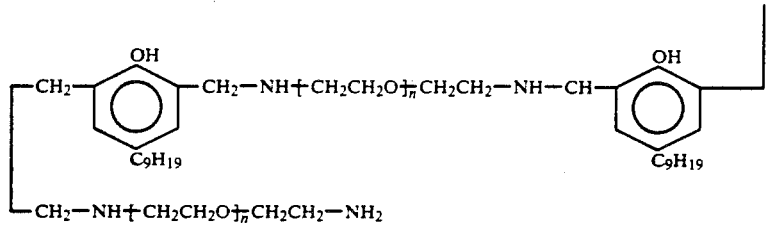

However, if the paired initial Mannich condensate of formula X is reacted with a stronger amine such as diethylenetriamine, rather than the polyoxyalkylenediamine, as shown, a significant "scrambling" takes place so that the amine of formula (II) is replaced to give products such as:

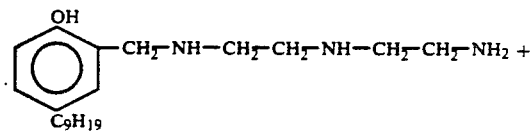

In a similar manner, if the bis-phenol is made from a dialkylpolyoxyalkylene diamine, the dialkylpolyoxyalkylene diamines are replaced with the unalkylated amine reactant. For example:

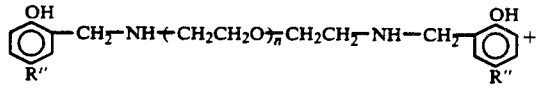

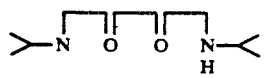

It is possible to mix the two disecondary amines but the reactions take much longer to go to completion. For example, when the product of Formula XIV is allowed to react with a bis-cyanoethyl ether, about 80% of the ortho groups react under the usual conditions used in the other examples, i.e.:

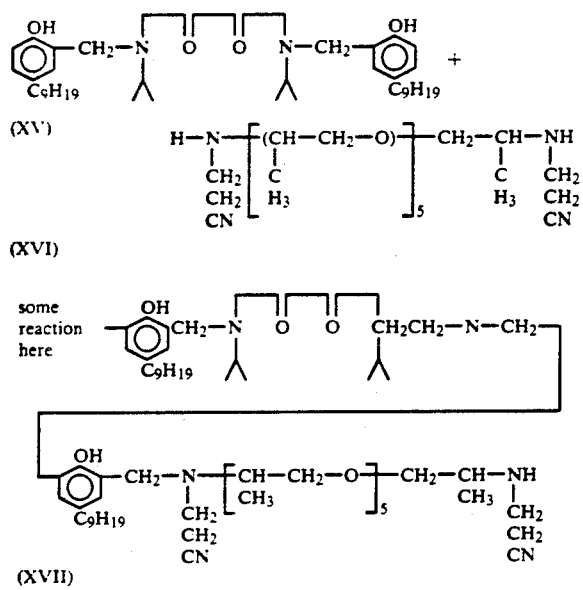

Utility of Mannich Condensates as Epoxy Curing Agents

The Mannich condensates of the present invention are useful as curing agents for 1,2-epoxy resins.

It is known to use amines such as aliphatic or aromatic amines for curing 1,2-epoxy resins as shown, for example, by Waddill U.S. Pat. No. 4,139,524 and Marquis et al. U.S. Pat. No. 4,162,358. See also, the textbook "Handbook of Epoxy Resins" by H. Lee and K. Neville, McGraw-Hill Book Company, 1967.

Generally the vicinal epoxide compositions that can be cured using the curing agents of this invention are organic materials having an average of more than one reactive 1,2-epoxide group. These polyepoxide materials can be monomeric or polymeric, saturated or unsaturated, aliphatic, cycloaliphatic, aromatic or heterocyclic, and may be substituted if desired with other substituents besides the epoxy groups, e.g., hydroxyl groups, ether radicals, halogenated phenyl groups and the like.

The most widely used epoxy resins are diglycidyl ethers of bisphenol A:

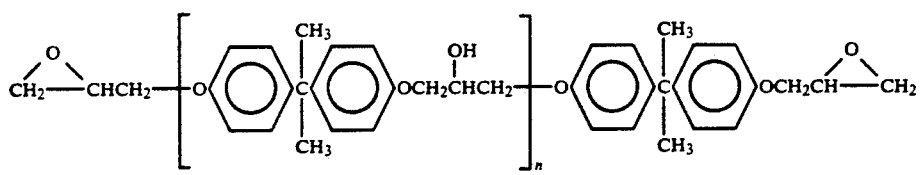

(XVIII)

where n equals an integer of up to about 10 to 20.

However, these epoxides are representative of the broader class of epoxides that are useful in making epoxy resins.

A widely used class of polyepoxides that can be cured includes the resinous epoxy polyethers obtained by reacting an epihalohydrin, such as epichlorohydrin, with either a polyhydric phenol or a polyhydric alcohol. An illustrative, but by no means exhaustive, listing of suitable dihydric phenols includes 4,4'-isopropylidene bisphenol, 2,4'-dihydroxydiphenylethylmethane, 3,3'-dihydroxydiphenyldiethylmethane, 3,4'-dihydroxydiphenylmethylpropylmethane, 2,3'-dihydroxydiphenylethylphenylmethane, 4,4'-dihydroxydiphenylmethane, 4,4'-dihydroxydiphenylbutylphenylmethane, 2,2'-dihydroxydiphenylditolylmethane, 4,4'-dihydroxydiphenyltolylmethyl-methane and the like. Other polyhydric phenols which may also be co-reacted with an epihalohydrin to provide these epoxy polyethers are such compounds as resorcinol, hydroquinone, substituted hydroquinones, e.g., tert-butylhydroquinone, and the like.

Among the polyhydric alcohols that can be co-reacted with an epihalohydrin to provide the resinous epoxy polyethers are such compounds as ethylene glycol, propylene glycol, butylene glycols, pentane diols, bis(4-hydroxycyclohexyl)dimethylmethane, 1,4-dimethylolbenzene, glycerol, 1,2,6-hexanetriol, trimethylclpropane, mannitol, sorbitol, erythritol, pentaerythritol, their dimers, trimers and higher polymers, e.g., polyethylene glycols, polypropylene glycols, triglycerol, dipentaerythritol and the like, polyallyl alcohol, polyhydric thioethers, such as 2,2'-, 3,3'-tetrahydroxydipropylsulfide and the like, mercapto alcohols such as α-monothioglycerol, α,α'-dithioglycerol, and the like, polyhydric alcohol partial esters, such as monostearin, pentaerythritol monoacetate, and the like, and halogenated polyhydric alcohols such as the monochlorohydrins of glycerol, sorbitol, pentaerythritol and the like.

Another class of polymeric polyepoxides that can be cured by means of the above-described curing agents includes the epoxy novolac resins obtained by reacting, preferably in the presence of a basic catalyst, e.g., sodium or potassium hydroxide, an epihalohydrin, such as epichlorohydrin, with the resinous condensate of an aldehyde, e.g., formaldehyde, and either a monohydric phenol, e.g., phenol itself, or a polyhydric phenol. Further details concerning the nature and preparation of these epoxy novolac resins can be obtained in H. Lee and K. Neville, "Handbook of Epoxy Resins".

It will be appreciated by those skilled in the art that the polyepoxide compositions that can be cured according to the practice of the present invention are not limited to the above described polyepoxides, but that these polyepoxides are to be considered merely as being representative of the class of polyepoxides as a whole.

The amount of curing agent that is employed in curing polyepoxide compositions will depend on the amine equivalent weight of the curing agent employed. The total number of equivalents of amine group is preferably from about 0.8 to about 1.2 times the number of epoxide equivalents present in the curable epoxy resin composition with a stoichiometric amount being most preferred.

Various conventionally employed additives can be admixed with these polyepoxide-containing compositions prior to final cure. For example, in certain instances it may be desired to add minor amounts of other co-catalysts, or hardeners, along with the curing agent system herein described. Conventional pigments, dyes, fillers, flame retarding agents and other compatible natural and synthetic resins can also be added. Further-more, known solvents for the polyepoxide materials such as acetone, methyl ethyl ketone, toluene, benzene, xylene, dioxane, methyl isobutyl ketone, dimethylformamide, ethylene glycol monoethyl ether acetate, and the like, can be used if desired, or where necessary.

SPECIFIC EXAMPLES

The invention will be further illustrated by the following specific examples which are given by way of illustration and not as limitations on the scope of this invention.

EXAMPLE 1

(6622-63) Mannich Adduct of p-Nonylphenol, Formaldehyde and N,N'-diisopropyl Triethylene Glycol Diamine To a 1-liter, three-necked flask equipped with a thermometer, a dropping funnel, a stirrer and nitrogen-inlet line was added p-nonylphenol (220 g, 1.0M) and 116 g, 0.5 mol of N,N'-diisopropyl triethylene glycol diamine. Then, formalin (37%, 81 g, 1.0M) was added dropwise at ca. 30° C. over a one hour period. The mixture was heated to 80° C. and held at this temperature for 4.0 hours and at 110° C. for two hours. During the process the generated water was removed through a Dean-Stark trap. The rest of the water was removed at less than 5 mm pressure at 110° C. The product was a viscous liquid. The analyses of total amine was 2.89 meq/g (theoretical 2.81 meq/g). The viscosity was 9600 cs/100° C. NMR spectra indicates the main product to be

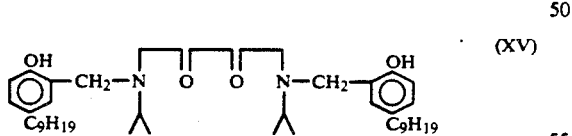

EXAMPLE 2

(6341-36) The Second Step of Mannich Adduct of Intermediate X from (6622-63) and N,N'-dicyanoethyl Polyoxypropylene Diamine The product of Example 1, 6622-33 (14 g.) was heated with 37% formalin (3.2 g) and 22 grams of the N,N'-diisopropyl derivative of a polyoxypropylene diamine (Jeffamine ® D-400) for four hours at 83°–88° C., then one hour at 120° C., and finally one hour at 120° C. and 0.3 mm pressure. About 80% of the product was believed to have the formula:

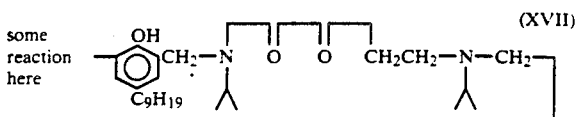

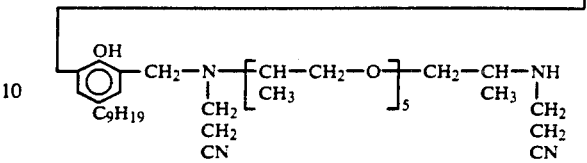

EXAMPLE 3

(6641-24) Preparation of Mannich Adduct from the bis-cyanoethyl Ether of Jeffamine ®-D-400

When 2 moles of formalin and 2 moles of p-nonylphenol were reacted with one mole of the bis-cyanoethyl ether of Jeffamine ®-D-400 at 122° C. and the water of reaction was removed, the expected bis-phenol product was produced, i.e.:

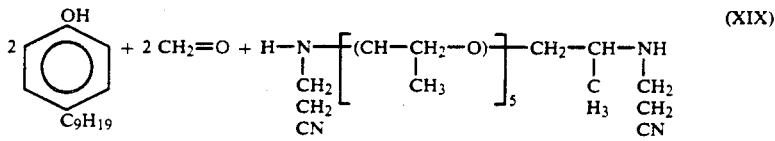

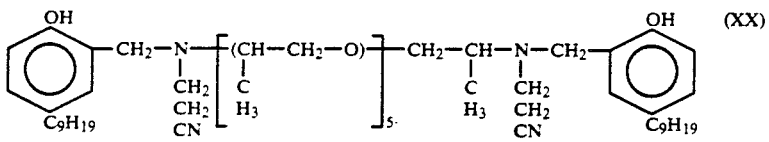

EXAMPLE 4

(6641-25) Comparative Example based on Example 3.

When the product of Example 3 (6641-24) was heated at 120° C. with two moles of triethyleneglycol diamine (Jeffamine ® EDR-148 amine) and two moles formaldehyde, the product was cleaved and the Mannich reaction product of Jeffamine ® EDR-148 amine, formaldehyde and p-nonyl-phenol was formed along with some novolaks.

EXAMPLE 5

(6322-63) Mannich Adduct of p-Nonylphenol, Formaldehyde and N,N'-diisopropyl EDR-148 (2:2:1 Molar Ratio)

To a 1 liter three-necked flask equipped with a thermometer, dropping funnel, mechanical stirrer, Dean-Stark trap and nitrogen-inlet line was charged nonylphenol (220 g, 1.0M) and N,N'-diisopropyl EDR-148 (116 g, 0.5M). Then, formalin (37%, 81 g, 1.0 mole) was added dropwise at ca. 25° C. The exothermic temperature was subsided by an ice/water bath. The addition process lasted about a 40 minute period of time. The mixture was heated and kept at 85°–90° C. for ca. 4 hours. The reaction temperature was raised to 110° C. and water was removed through a Dean-Stark trap. At 110° C. the mixture was subjected to a vacuum to remove trace amounts of water. The product was recovered (347 g) as transparent, light-colored, viscous liquid. The analyses showed the total amine content as 2.89 meq/g (calc. 2.86 meq/g) and viscosity was 9600 cs/100° C.

The H'nmr indicated the Structure A

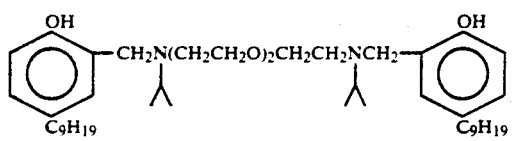

EXAMPLE 6

(6322-36) (Comparative) Mannich Adduct of Phenol, Formaldehyde and N,N'-diisopropyl EDR-148 (2:2:1 Molar Ratio)

The experimental procedures of Example 5 (6322-63) were repeated except using phenol (94 g, 1 mole), formalin (37%, 81 g, 1 mole) and N,N'-diisopropyl EDR-148 (116 g, 0.5M). The resulting product was viscous liquid.

EXAMPLE 7

(6322-60) (Comparative) Second Step Mannich of Product 6322-36 with EDR-148 as Terminating Amine To a 250 ml three-necked flask equipped with a thermometer, Dean-Stark trap, dropping funnel, stirrer and nitrogen line was charged product 6322-36 adduct of phenol, formaldehyde and N,N'-diisopropyl EDR-148 (0.12M) and EDR-148 (36 g, 0.24 mole). Then, formalin (19 g, 0.24 mole) was added dropwise over a 10 minute period. The mixture was heated to 80° C. for four hours then removed water at 110°-130° C. The product was gelled material. It is demonstrated the corresponding phenol product cannot be made under these conditions.

The foregoing examples are given by way of explanation and are not intended as limitations on the scope of the invention disclosed herein, as described in the appended claims.

We claim:

1. A compound of the formula:

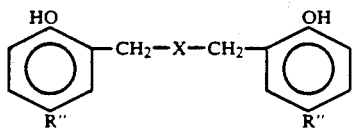

wherein X represents a polyoxyalkylene amine group having the formula:

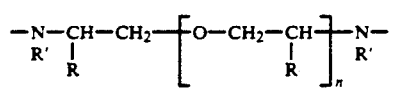

wherein:

n represents a positive number having a value of 1 to 6,

R represents hydrogen or methyl,

R' represents a cyanoethyl group, and

R" represents a straight chain or branched alkyl group containing from 1 to 15 carbon atoms.

2. A compound of the formula:

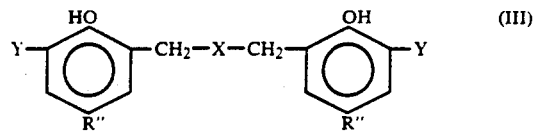

wherein X represents a group having the formula:

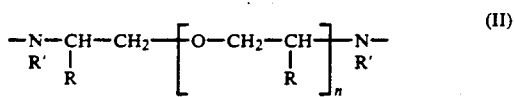

wherein Y represents a group having the formula:

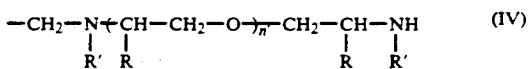

wherein:

n represents a positive integer having a value of 1 to 6, n' represents a positive integer having a value of 1 to 6, R represents hydrogen or methyl, R' represents a straight chain or branched alkyl group containing from 1 to 4 carbon atoms or a cyanoethyl group, and R" represents a straight chain or branched alkyl group containing from 1 to 15 carbon atoms.

3. A compound as in claim 2 wherein R represents H and R' represents a cyanoethyl group.

4. A compound as in claim 2 wherein R represents H and R' represents an alkyl group containing 1 to 4 carbon atoms.

5. A compound as in claim 2 wherein R represents H and R' represents an isopropyl group.

6. A compound as in claim 2 wherein R represents methyl and R' represents a cyanoethyl group.

7. A compound as in claim 2 wherein R represents methyl and R' represents an alkyl group containing 1 to 4 carbon atoms.

8. A compound as in claim 2 wherein R represents methyl and R' represents an isopropyl group.

9. A compound as in claim 2 wherein R in formula (II) represents H, R' in formula (II) represents an isopropyl group, R" represents an alkyl group containing 9 carbon atoms, R in formula (IV) represents methyl and R' in formula (IV) represents a cyanoethyl group.

* * * * *